US012558557B2

(12) United States Patent (10) Patent No.: US 12,558,557 B2
Prutchi et al. (45) Date of Patent: Feb. 24, 2026

(54) DISCRIMINATION OF SUPRAVENTRICULAR TACHYCARDIAS IN COMBINED CCM-ICD DEVICE

(71) Applicant: Impulse Dynamics NV, Willemstad (CW)

(72) Inventors: David Prutchi, Voorhees, NJ (US); Jason Meyers, Haddonfield, NJ (US)

(73) Assignee: Impulse Dynamics NV

( * ) Notice: Subject to any disclaimer, the term of this patent is extended or adjusted under 35 U.S.C. 154(b) by 599 days.

(21) Appl. No.: 17/424,981

(22) PCT Filed: Jan. 23, 2020

(86) PCT No.: PCT/IB2020/050534
§ 371 (c)(1),
(2) Date: Jul. 22, 2021

(87) PCT Pub. No.: WO2020/152619
PCT Pub. Date: Jul. 30, 2020

(65) Prior Publication Data
US 2022/0088402 A1 Mar. 24, 2022

Related U.S. Application Data

(60) Provisional application No. 62/795,612, filed on Jan. 23, 2019.

(51) Int. Cl.
*A61N 1/39* (2006.01)
*A61N 1/05* (2006.01)
(Continued)

(52) U.S. Cl.
CPC .............. *A61N 1/3956* (2013.01); *A61N 1/05* (2013.01); *A61N 1/3622* (2013.01); *A61N 1/3682* (2013.01)

(58) Field of Classification Search
CPC ...... A61N 1/05; A61N 1/3622; A61N 1/3682; A61N 1/3956
See application file for complete search history.

(56) References Cited

U.S. PATENT DOCUMENTS 4,754,753 A 7/1988 King
5,181,511 A * 1/1993 Nickolls .............. A61N 1/3622
607/4
(Continued)

FOREIGN PATENT DOCUMENTS

JP 2008-515486 5/2008
WO WO 2004/050185 6/2004
(Continued)

OTHER PUBLICATIONS

Notice of Reason(s) for Rejection Dated Sep. 2, 2023 From the Japan Patent Office Re. Application No. 2021-542190 and Its Translation Into English. (12 Pages).
(Continued)

*Primary Examiner* — William J Levicky

(57) ABSTRACT
During a cardiac arrhythmia, defibrillation shocks from an implanted cardiac defibrillator are suppressed based on the sensing of electrical wavefront arrival times which indicate a supraventricular origin to the cardiac arrhythmia. In some embodiments, times of electrical wavefront arrival in at least two ventricular locations of the heart are sensed; one location being relatively superior, and one relatively inferior (e.g., relatively superior and inferior locations of a ventricular septum). In some embodiments, if the arrival time at the more inferior position is within a predetermined interval after arrival at the more superior position, delivery of defibrillation shocks are suppressed. In some embodiments, additional sensing of electrical wavefront arrival at one or more non-septal ventricular locations is performed, and defibrillation shock suppression is optionally itself sup-
(Continued)

pressed if the additional sensing indicates that the wavefront initiated in a ventricular location.

31 Claims, 8 Drawing Sheets

(51) Int. Cl.

| | | |
|---|---|---|
| *A61N 1/362* | (2006.01) | |
| *A61N 1/368* | (2006.01) | |

(56) References Cited

U.S. PATENT DOCUMENTS

| | | | | |
|---|---|---|---|---|
| 5,193,535 | A * | 3/1993 | Bardy | A61N 1/3621 |
| | | | | 607/129 |
| 5,263,977 | A * | 11/1993 | Adams | A61N 1/056 |
| | | | | 607/122 |
| 5,325,856 | A * | 7/1994 | Nitzsche | A61N 1/3621 |
| | | | | 600/516 |
| 6,263,242 | B1 | 7/2001 | Mika et al. | |
| 6,993,385 | B1 * | 1/2006 | Routh | A61N 1/3621 |
| | | | | 607/4 |
| 2003/0009197 | A1 * | 1/2003 | Helland | A61N 1/368 |
| | | | | 607/9 |
| 2003/0023130 | A1 | 1/2003 | Ciaccio et al. | |
| 2004/0111119 | A1 | 6/2004 | Sarkar et al. | |
| 2006/0074330 | A1 * | 4/2006 | Smith | A61N 1/3622 |
| | | | | 600/515 |
| 2006/0247687 | A1 | 11/2006 | Swerdlow et al. | |
| 2009/0099618 | A1 * | 4/2009 | Rousso | A61N 1/368 |
| | | | | 607/9 |
| 2009/0143832 | A1 | 6/2009 | Saba | |
| 2009/0306731 | A1 | 12/2009 | Doerr | |
| 2010/0087881 | A1 | 4/2010 | Shuros et al. | |
| 2010/0249626 | A1 | 9/2010 | El Arab et al. | |
| 2012/0041508 | A1 | 2/2012 | Rousso | |
| 2014/0148868 | A1 * | 5/2014 | Saba | A61N 1/36592 |
| | | | | 600/518 |
| 2016/0235964 | A1 | 8/2016 | Rousso et al. | |
| 2019/0143832 | A1 | 5/2019 | Birek et al. | |

FOREIGN PATENT DOCUMENTS

| | | |
|---|---|---|
| WO | WO 2006/039694 | 4/2006 |
| WO | WO 2018/197865 | 11/2018 |
| WO | WO 2020/152619 | 7/2020 |

OTHER PUBLICATIONS

Translation Dated Apr. 27, 2022 of Notification of Office Action Dated Mar. 26, 2022 From the State Intellectual Property Office of the People's Republic of China Re. Application No. 202080006541. 9. (9 Pages).

Notification of Office Action and Search Report Dated Jan. 14, 2022 From the State Intellectual Property Office of the People's Republic of China Re. Application No. 202080006541.9. (11 Pages).

English Translation Dated Feb. 17, 2022 of Notification of Office Action and Search Report Dated Jan. 14, 2022 From the State Intellectual Property Office of the People's Republic of China Re. Application No. 202080006541.9. (7 Pages).

Translation Dated Aug. 5, 2022 of Notification of Office Action Dated Jul. 20, 2022 From the China National Intellectual Property Administration Re. Application No. 202080006541.9. (4 Pages).

Notification of Office Action and Search Report Dated Mar. 26, 2022 From the State Intellectual Property Office of the People's Republic of China Re. Application No. 202080006541.9. (13 Pages).

International Search Report and the Written Opinion Dated May 26, 2020 From the International Searching Authority Re. Application No. PCT/IB2020/050534. (13 Pages).

Notification of Office Action Dated Jul. 20, 2022 From the China National Intellectual Property Administration Re. Application No. 202080006541.9. (7 Pages).

International Preliminary Report on Patentability Dated Aug. 5, 2021 From the International Bureau of WIPO Re. Application No. PCT/IB2020/050534. (8 Pages).

Notice of Reason(s) for Rejection Dated Apr. 16, 2024 From the Japan Patent Office Re. Application No. 2021-542190 and Its Translation Into English. (9 Pages).

Communication Pursuant to Article 94(3) EPC Dated Dec. 21, 2023 From the European Patent Office Re. Application No. 20704078.3. ( 4 Pages).

\* cited by examiner

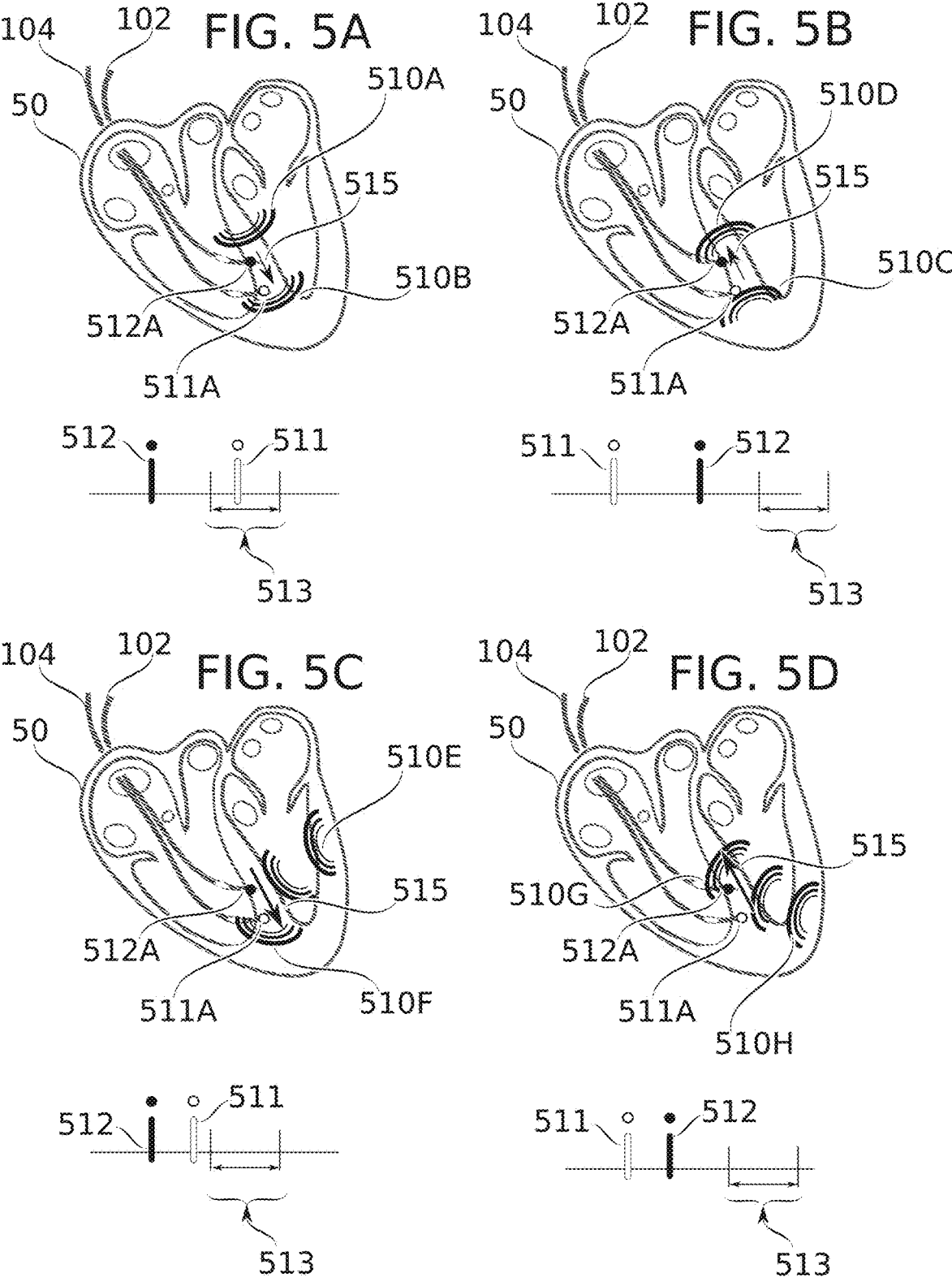

610

Place electrodes in heart septal wall

612

Measure relative wavefront delay

614

Select discrimination window, based on wavefront delay

DISCRIMINATION OF SUPRAVENTRICULAR TACHYCARDIAS IN COMBINED CCM-ICD DEVICE

RELATED APPLICATIONS

This application is a National Phase of PCT Patent Application No. PCT/IB2020/050534 having International filing date of Jan. 23, 2020, which claims the benefit of priority under 35 USC § 119(e) of U.S. Provisional Patent Application No. 62/795,612 filed Jan. 23, 2019, the contents of which are incorporated herein by reference in their entirety.

FIELD AND BACKGROUND OF THE INVENTION

The present invention, in some embodiments thereof, relates to the field of implanted cardiac devices and more particularly, to the control of heart pacing using implanted cardiac devices.

The use of implantable cardioverter defibrillators (ICDs) is commonplace in patients with chronic heart failure (CHF). ICDs have significantly reduced mortality among these patients, and ICD therapy is recommended for primary prevention to reduce total mortality by reducing sudden cardiac death (SCD) in CHF patients with a left-ventricular ejection fraction (LVEF) under 35%.

Mika et al. in U.S. Pat. No. 6,263,242 "Apparatus and method for timing the delivery of non-excitatory ETC signals to a heart" describe CCM signals delivered to cardiac tissue when the intrinsic depolarization wave sweeping through the ventricles is detected within a specific timing relationship between two electrode sites.

SUMMARY OF THE INVENTION

There is provided, in accordance with some embodiments of the present disclosure, a method of controlling an input to an implanted heart device in response to a heart arrhythmia, the method comprising: sensing, during a cardiac arrhythmia in a heart, a direction of electrical wavefront passage through a ventricular region of the heart; and providing an input to the implanted heart device, based on the sensed direction of the electrical wavefront.

In some embodiments, the implanted heart device is configured to apply antiarrhythmic therapy, and comprising configuring the implanted heart device to apply the antiarrhythmic therapy using the provided input.

In some embodiments, the implanted heart device comprises a defibrillator, and comprising configuring the defibrillator for production of defibrillation shocks using the provided input.

In some embodiments, the ventricular region of the heart comprises a ventricular septum.

According to some embodiments of the present disclosure, the sensing includes using calibration information to determine the direction of electrical wavefront passage.

In some embodiments, the sensing comprises sensing relative timing of the passage of the electrical wavefront through a plurality of locations within the ventricular region.

In some embodiments, each of the plurality of locations is defined by the location of an electrode pair used to perform the sensing.

In some embodiments, the controlling comprises preventing production of defibrillation shocks when the sensed direction of electrical wavefront passage indicates that the electrical wavefront is traveling in a direction from the atria and toward the ventricles.

In some embodiments, the sensing the direction comprises sensing times of electrical wavefront arrival in at least two ventricular locations of the heart; and the provided input is an indication to the implanted heart device to configure application of antiarrhythmic therapy based on the relative timing of the sensing at the at least two locations.

In some embodiments, the at least two locations comprise two locations along a ventricular septum.

In some embodiments, the at least two locations along the ventricular septum are separated by at least 1 cm.

In some embodiments, the two locations along the ventricular septum are arranged along a superior-inferior axis extending along the ventricular septum.

In some embodiments, each of the at least two locations is defined by the location of an electrode pair.

In some embodiments, each electrode pair is positioned on a separate lead.

In some embodiments, a plurality of electrode pairs are positioned on a single lead.

In some embodiments, at least one electrode is used of a member of a plurality of electrode pairs.

In some embodiments, the implanted heart device is an at least dual function device.

In some embodiments, the implanted heart device comprises a cardiac contractility modulation (CCM) therapy device.

In some embodiments, electrodes on leads used for cardiac sensing and/or therapeutic current delivery for CCM therapy by the CCM therapy device are also used for sensing electrical wavefront arrival in the at least two locations.

In some embodiments, the direction of the electrical wavefront is in a direction from the atria and toward the ventricles, and the input is used to suppress delivery of the antiarrhythmic therapy.

In some embodiments, the at least two locations are at different positions along a superior-inferior axis, and suppressing input is provided when the electrical wavefront is sensed to arrive at the more superior location before arriving at a more inferior location.

In some embodiments, deliver of the antiarrhythmic therapy is not suppressed input if the electrical wavefront arrives at the more inferior location before a predetermined delay elapses from the time of arrival at the more superior location.

In some embodiments, the at least two locations comprises a non-septal location in the ventricles.

In some embodiments, the provided input acts to suppress delivery of the antiarrhythmic therapy when electrical wavefront is sensed to arrive at a more superior location in the ventricular septum before arriving at a more inferior location in the ventricular septum, unless the time of electrical wavefront arrival at the non-septal location in the ventricles is within a predetermined interval before the electrical wavefront is sensed to arrive within the ventricular septum.

There is provided, in accordance with some embodiments of the present disclosure, an implantable cardioverter defibrillator device (ICD) configured to: sense, during a cardiac arrhythmia in a heart and within the interval of a heartbeat, times of electrical wavefront arrival in at least two ventricular locations of the heart; and suppress production of defibrillation shocks by the defibrillator in response to the cardiac arrhythmia, based on the relative timing of the sensing at the at least two locations.

In some embodiments, the device comprises at least two bipolar sensing electrodes.

In some embodiments, the at least two bipolar sensing electrodes are configured to be attached to locations along the ventricular septum.

In some embodiments, the at least two bipolar sensing electrodes are on separate leads.

In some embodiments, the device also is configured to perform cardiac contractility modulation (CCM) therapy using the electrodes on the separate leads.

In some embodiments, the at least two bipolar sensing electrodes are on a single lead of the ICD.

In some embodiments, the single lead of the ICD is configured to be implanted extending along the ventricular septum.

In some embodiments, the at least two bipolar sensing electrodes are configured to be positioned at different locations along a superior-inferior axis within a ventricular septum, and the ICD suppresses production of defibrillation shocks when the electrical wavefront is sensed to arrive at the more superior location before arriving at a more inferior location.

In some embodiments, the device comprises a sensing electrode configured to be positioned in a non-septal location of the ventricles.

In some embodiments, the device is configured so that the production of defibrillation shocks is not suppressed if the sensing electrode configured to be positioned in a non-septal location of the ventricles senses electrical wavefront arrival within a predetermined interval before the ICD senses arrive of the electrical wavefront at a ventricular septum location.

According to an aspect of some embodiments of the present disclosure, there is provided a method of controlling an input to an implanted heart device in response to a heart arrhythmia, the method including: receiving an input from a first electrode and a second electrode implanted within a ventricular region of the heart; using calibration information to determine a direction of an electrical wavefront moving between the first and second electrodes; and providing an input to the implanted heart device, based on the sensed direction of the electrical wavefront.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system" (e.g., a method may be implemented using "computer circuitry"). Furthermore, some embodiments of the present disclosure may take the form of a computer program product embodied in one or more computer readable medium(s) having computer readable program code embodied thereon. Implementation of the method and/or system of some embodiments of the present disclosure can involve performing and/or completing selected tasks manually, automatically, or a combination thereof. Moreover, according to actual instrumentation and equipment of some embodiments of the method and/or system of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In some embodiments of the present disclosure, one or more tasks performed in method and/or by system are performed by a data processor (also referred to herein as a "digital processor", in reference to data processors which operate using groups of digital bits), such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the present disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. A computer readable storage medium may also contain or store information for use by such a program, for example, data structured in the way it is recorded by the computer readable storage medium so that a computer program can access it as, for example, one or more tables, lists, arrays, data trees, and/or another data structure. Herein a computer readable storage medium which records data in a form retrievable as groups of digital bits is also referred to as a digital memory. It should be understood that a computer readable storage medium, in some embodiments, is optionally also used as a computer writable storage medium, in the case of a computer readable storage medium which is not read-only in nature, and/or in a read-only state.

Herein, a data processor is said to be "configured" to perform data processing actions insofar as it is coupled to a computer readable memory to receive instructions and/or data therefrom, process them, and/or store processing results in the same or another computer readable storage memory. The processing performed (optionally on the data) is specified by the instructions. The act of processing may be referred to additionally or alternatively by one or more other terms; for example: comparing, estimating, determining, calculating, identifying, associating, storing, analyzing, selecting, and/or transforming. For example, in some embodiments, a digital processor receives instructions and data from a digital memory, processes the data according to the instructions, and/or stores processing results in the digital memory. In some embodiments, "providing" processing results comprises one or more of transmitting, storing and/or presenting processing results. Presenting optionally comprises showing on a display, indicating by sound, printing on a printout, or otherwise giving results in a form accessible to human sensory capabilities.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings:

FIGS. 5A-5D schematically illustrate discrimination of conduction patterns passing through a ventricular septum, according to some embodiments of the present disclosure;

Figure 1A:
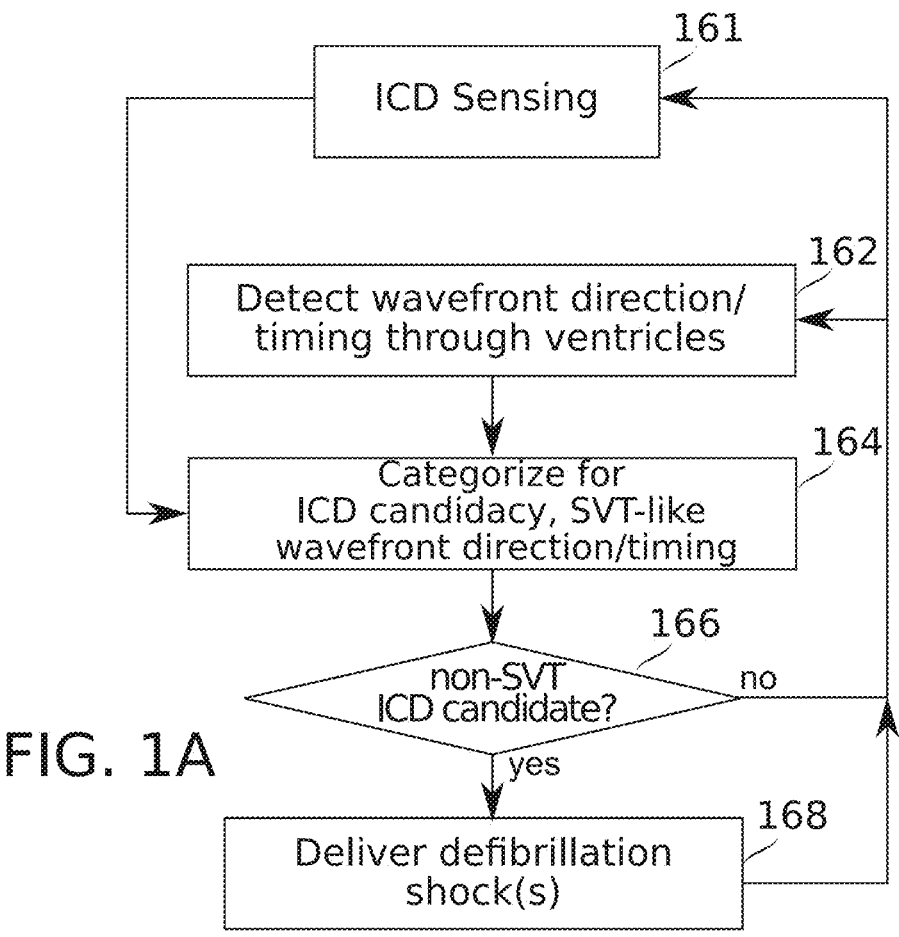
FIG. 1A schematically represents a method of discriminating SVT-type arrhythmias which otherwise would be apparent candidates for defibrillation by an ICD device, according to some embodiments of the present disclosure.

DESCRIPTION OF SPECIFIC EMBODIMENTS
OF THE INVENTION

The present invention, in some embodiments thereof, relates to the field of implanted cardiac devices and more particularly, to the control of heart pacing using implanted cardiac devices.

Overview

An aspect of some embodiments of the current invention relates to distinguishing types of arrhythmic heartbeat patterns in response to which an implantable cardioverter defibrillator device (ICD) should or should not deliver a shock. In some embodiments, for example, ventricular tachycardia (VT) is preferably corrected by the action of an ICD, while supraventricular tachycardia (SVT) (or another pattern) preferably is not.

An ICD, though potentially life-saving, can also create severe intrusions into a patient's life when its shocks are administered in response to heart arrhythmias (optionally, tachyarrhythmia more specifically) which do not require immediate intervention. Herein, such shocks are referred to as "unnecessary shocks".

Clinical studies have suggested that up to 13% of patients who receive an ICD may receive unnecessary shocks. This potentially leads to pain, anxiety, and other effects detrimental to the patient's health and/or well-being. As shown in the following table, large clinical studies with ICDs have shown that as many as 20% to 40% of total shocks are "unnecessary", since they are delivered to terminate non-life-threatening or non-severely symptomatic arrhythmias.

| TRIAL | INCIDENCE OF UNNECESSARY SHOCKS |
|---|---|
| SCD HeFT | 32% |
| SCD-MADIT II | 36.4% |
| AVID | 21% |

Nearly 80% of unnecessary shocks have been reported to be caused by supra-ventricular tachycardia (SVT), a group of tachyarrhythmias which includes: atrial fibrillation (AF), atrial flutter, sinus tachycardia, atrial tachycardia, atrioventricular (AV) reentrant tachycardia, and AV nodal re-entrant tachycardia (AVNRT). This was well documented, for example, in the results of the MADIT II study (Daubert et al., J Am Coll Cardiol, 51(14), 2008), in which shocks were found to have been unnecessarily delivered by ICDs due to the following causes:

| REASON | INCIDENCE |
|---|---|
| Atrial Fibrillation | 44% |
| Other SVT | 36% |
| Abnormal Sensing | 20% |

To reduce the incidence of unnecessary shocks, algorithms have been developed based on the analysis of rhythm irregularity and other factors to facilitate discrimination and avoidance of the unnecessary delivery of ICD shocks on SVTs. However, several SVT types potentially occur with a 1:1 A-V relationship, thereby presenting a potential diagnostic challenge when assessed through analysis of rhythm alone.

In an effort to improve upon the discrimination of true-ventricular tachycardia from supraventricular tachycardia based on rate stability criteria, some devices make use of signals sensed directly from the atria. However, this requires the implantation of an additional lead (an atrial pacing/sensing lead) or the use of a specialized "single-pass" lead with floating atrial sense electrodes.

Single-chamber ICDs (those which are connected to the heart via a single ventricular lead) have made use of morphological analysis of the intracardiac electrogram (IEGM) signal to aid in discriminating VTs from SVTs. This is because the shape of the IEGM propagating through the normal ventricular conduction system, and thus originating at the AV node, is generally different than that recorded when the ventricular beats originate within the ventricle.

However, morphological analysis increases the use of computational power, which is potentially scarce in an implantable device subject to power use constraints. Furthermore, morphology has commonly been analyzed through the near-field channel (bipolar sensing). This channel is prone to indicating locally-appropriate conduction, which may mischaracterize a conduction pattern which is abnormal for the ventricles as a whole.

Devices may apply a morphology discriminator to a channel with more widely-spaced electrodes, potentially overcoming the near-field problem; but this has the drawback of a noisier signal (e.g. disturbed by myopotentials, movement, and electromagnetic interference). This potentially limits its ability to discriminate tachyarrhythmias by type; e.g., to distinguish true VTs from SVTs.

Devices configured to provide cardiac contractility modulation (CCM) therapy may be provided with a plurality of leads (e.g., two) which can be implanted to the cardiac tissue (e.g., the septal wall) and configured to sense electrical signals propagating therethrough. In some embodiments, the leads are spaced (e.g., separated by at least 1 cm, 2 cm, or another distance) along an axis which is substantially parallel to the direction of propagation of a cardiac conduction wavefront passing between the two leads.

In some embodiments of the present invention, propagation time and/or propagation paths of depolarization wavefronts are detected through a plurality of right-ventricular septum leads that are commonly used in cardiac contractility modulation (CCM) therapy. In some embodiments, the leads are arranged along a superior-inferior axis (e.g., arranged separated by at least 1 cm, 2 cm, or another distance). This axis corresponds, in some embodiments, to an axis along which transmission initiated supraventricularly normally travels as it passes through the septum.

Detections through the plurality of leads are analyzed to provide tachyarrhythmia type discrimination, for example, discrimination distinguishing SVT from VT. Optionally, a device capable of providing CCM is also configured to act as an ICD to provide defibrillation therapy, and/or to provide sensing and/or discrimination input to an ICD. In some embodiments, the detection uses an event-triggered windowing algorithm, which discriminates whether detected wavefront events at different sensing locations during tachyarrhythmia occur with an order and/or timing that is consistent with SVT, or with an order and/or timing which alternatively is more likely indicative of ventricular tachycardia.

Potentially, the method prevents inappropriate, unnecessary shock therapy due to rapid SVT conduction, by allowing tachyarrhythmia of the SVT type to be distinguished and excluded as a shock therapy trigger. This method is optionally implemented with little increased demand on the restricted levels of power and/or computational resources normally available in a device capable of CCM signal delivery.

In some embodiments, detection of SVT is used to provide an input affecting application of a treatment other than a shock therapy appropriate to VT.

Herein, embodiments are described with regard to the example of controlling of defibrillation shocks delivered by an ICD implantable heart device. However, it should be understood that electrode sensing of wavefront direction is additionally or alternatively used in configuring the application of antiarrhythmic therapy in other types of devices, for example, atrium-sensed atrium pacing (AA pacing), inhibitory conditioning, and/or cardioversion. Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Method of Discriminating SVT-type Arrhythmia

Reference is now made to FIG. 1A, which schematically represents a method of discriminating SVT-type arrhythmia during tachyarrhythmia which otherwise would be an apparent candidate for defibrillation by an ICD device, according to some embodiments of the present disclosure.

The initial blocks of the flowchart are presented in two, optionally sequential or parallel sensing operations. At block 161, in some embodiments, ICD sensing is performed. This comprises measuring signals from one or more heart-implanted leads to yield data which potentially indicate that a heart arrhythmia event is occurring which is a potential candidate for triggering shock therapy.

At block 162, in some embodiments, sensing to detect a direction of wavefront propagation through a region of the ventricles is performed. Optionally, the direction of wavefront propagation is determined from a sensed relative timing of heart electrical activity waveforms reaching a plurality of electrodes at different times, for example as described in relation to FIGS. 1C-1D, FIG. 2, and/or FIGS. 5A-5D, herein. Different relative timings of detection potentially correspond to different directions. Direction analysis is optionally not to an exact direction; but rather performed to a sufficient degree to categorize the event at block 164. For example, direction may simply be detected as comprising a clear superior to inferior component (like an SVT event), or not (like a VT event).

Furthermore, direction determination as such does not necessarily occur as an explicit step, and does not necessarily include providing a separate "directionality" output. For example, a timing difference indicated from sensing at block 162 is optionally used to directly determine an SVT or VT categorization at block 164. The directionality determination is nevertheless implicit in this categorization, as the underlying basis for the timing difference indicating SVT or VT is because there is a different direction of wavefront propagation for these two categories. Accordingly, portions of the direction determination of block 162 are optionally performed as part of block 164, e.g., as part of the SVT/VT categorization itself.

At block 166, in some embodiments, categorization of the sensing of block 161 and/or the wavefront direction detection at block 164 is performed. The result of the categorizations is a determination of the existence of heart arrhythmia, and furthermore, analysis of wavefront directionality to infer whether or not the heart arrhythmia appears to be supraventricular in origin; that is, due to supraventricular tachycardia (SVT), or not.

In particular, the existence of heart arrhythmia (a heart arrhythmia event) may be detected as a severe tachycardia within heart ventricle(s), corresponding to a heart rate over, for example, 160 bpm, 170 bpm, 180 bpm, 190 bpm, and/or over 200 bpm. Optionally, the heart rate window for shock therapy triggers is also below a higher heart rate; for example, a candidate ventricular arrhythmia is less than 250 bpm. Higher heart rate ventricular arrhythmias are optionally considered to be ventricular fibrillations, and treated differently.

Optionally, directionality analysis at block 164 is skipped if there is no current tachyarrhythmia which is a candidate event for distinguishing between SVT and VT arrhythmia types. Optionally, block 162 is only performed in order to allow directionality and/or timing analysis if there is a current tachyarrhythmia.

At block 166, the flowchart branches, depending on whether or not there is a detected arrhythmia which is not an SVT arrhythmia. If so, then at block 168, ne or more defibrillation shocks is delivered. Otherwise, delivery of defibrillation shocks does not occur. In either case, the flowchart returns to the sensing/detection of blocks 161, 162.

Figure 1B:
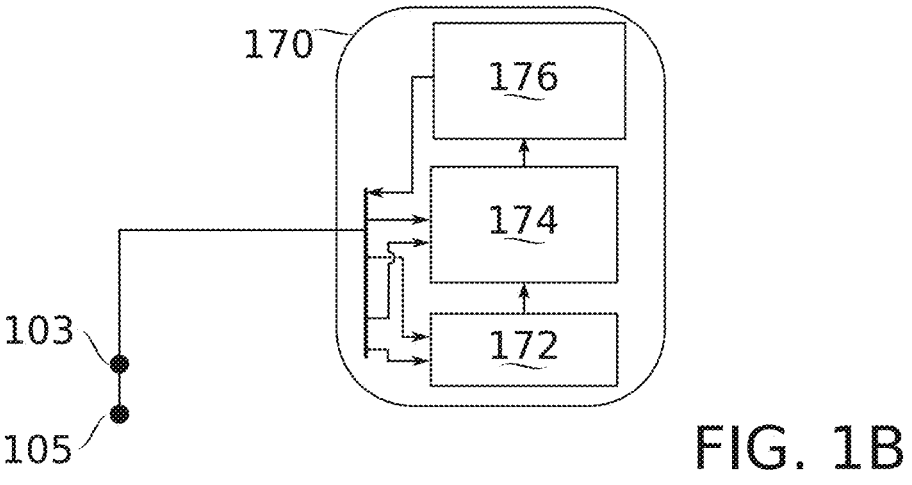
FIG. 1B is a block diagram that schematically represents an ICD device configured to discriminate SVT-type arrhythmias based on inputs from two ventricular electrode sets.
Figure 1C:
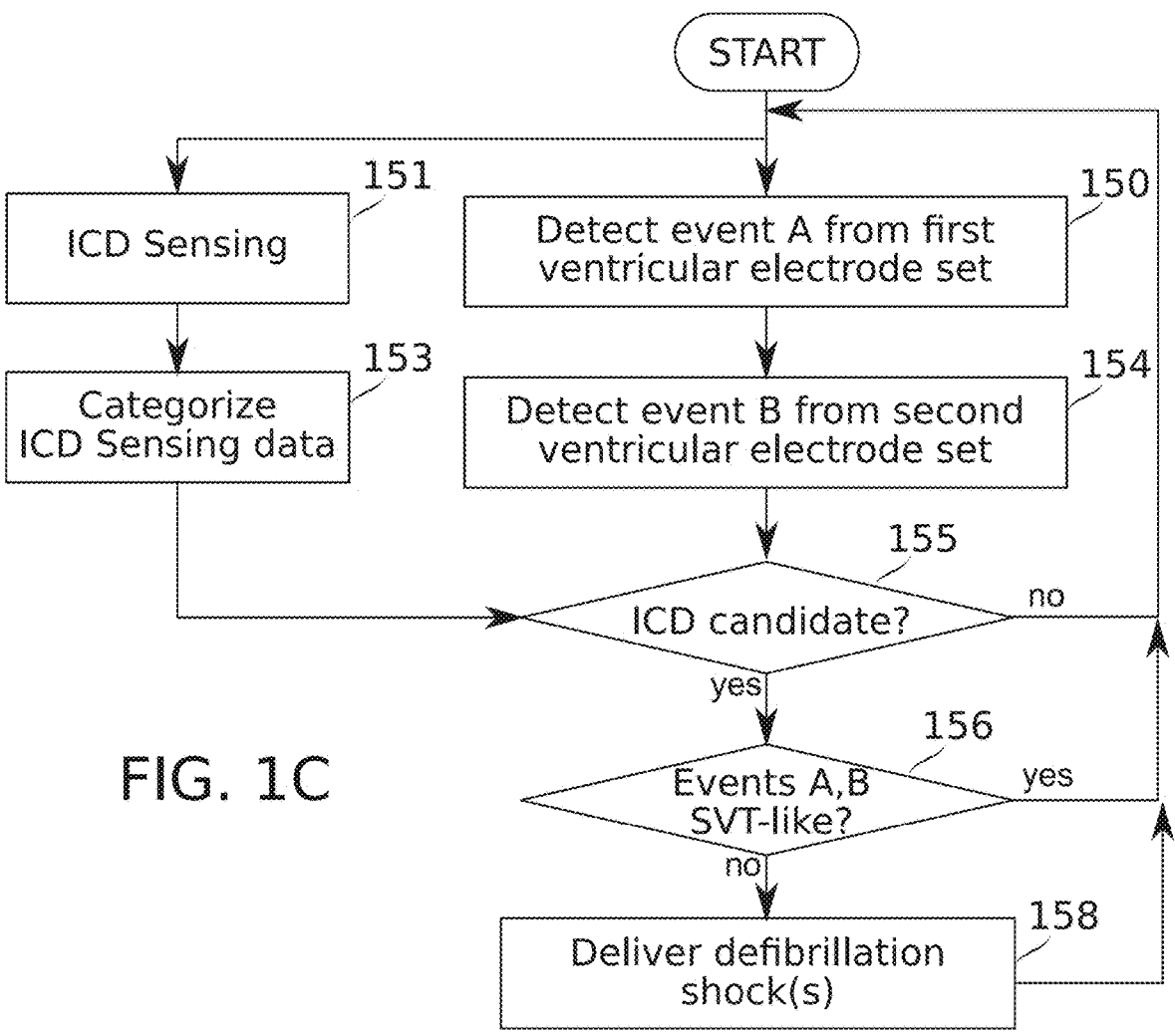
FIG. 1C schematically represents a more specific method of discriminating SVT-type arrhythmias which otherwise would be apparent candidates for defibrillation by an ICD device, according to some embodiments of the present disclosure.

Reference is now made to FIG. 1C, which schematically represents a more particular method of discriminating SVT-type arrhythmias which otherwise would be apparent candidates for defibrillation by an ICD device, according to some embodiments of the present disclosure. The method of FIG. 1C may be understood as describing particular embodiments implementing the method of FIG. 1A; with the operations of the two corresponding, for example, as described hereinbelow.

The initial blocks of the flowchart are presented in two parallel processing streams. Along one processing stream and at block 151, in some embodiments, ICD sensing is performed. This comprises measuring signals from one or more heart-implanted leads to yield data which potentially indicate that a heart arrhythmia event is occurring. In some embodiments, block 151 corresponds to block 161 of FIG. 1A. At block 153, in some embodiments, the ICD sensing data are categorized as indicating or not indicating a heart arrhythmia (e.g., as described in relation to block 161), and at block 155, a determination is made as to whether or not the heart arrhythmia represents a candidate condition for defibrillation. Blocks 153, 155 may be understood as comprising part of the operations described in relation to block 164 of FIG. 1A, in some embodiments.

Along the other processing stream and at block 150, in some embodiments, a first event A is detected from a first ventricular electrode set (e.g., a plurality of electrodes arranged to perform near-field sensing). At block 154, in some embodiments, a second event B is detected from a second ventricular electrode set. Herein, the term "near-field sensing" refers to sensing which is dominated by electrical field gradients extending through a region located at and between electrodes of an electrode set. In some embodiments, the operations of blocks 150, 154 correspond to the operations of block 162 of FIG. 1A.

Detection of the relative timing of wavefront events at two different positions (e.g., by two different ventricular electrode sets) is used, in some embodiments, in the estimation of a direction of wavefront travel between the two positions. In a simple form, the estimated direction of wavefront travel is "from" the earliest-detecting position "to" the later detecting position. The wavefront could travel at an angle oblique or perpendicular to a joining axis drawn between the two positions, and in this case the direction of wavefront travel can optionally be estimated by their relative timing. For example, if corresponding events are measured simultaneously at two positions, the waveform is optionally estimated to be travelling in a direction perpendicular to their joining axis. In some embodiments, the direction of wavefront travel is constrained to the set of directions consistent with both a physiologically plausible wavefront velocity, and the relative timing of wavefront-associated events measured at the two positions. Optionally, three or more sensing positions are used, which can help to further refine estimates of the direction of wavefront propagation.

The at least first and second ventricular electrode sets are "ventricular" insofar as they are placed in the ventricles so that they sense electrical impulses (also referred herein as "depolarization wavefronts") that control heart contraction at places where these electrical impulses propagate through ventricular heart wall regions. In some embodiments, the first and second ventricular electrode sets are, more specifically, implanted to the heart, e.g., a septal wall of the heart, so that they perform sensing of localized signals within the ventricular septum, at two respective separate locations.

Optionally, the ventricular electrode sets partially overlap in their member electrodes; e.g., a central electrode is optionally shared among each of the two electrodes sets. For purposes of description, methods and systems herein are described with respect to two ventricular electrode sets; however it should be understood that three or more ventricular electrode sets are optionally used. Optionally, the ventricular electrode sets are on two different leads, or three or more leads. A two lead configuration has particular relevance, in some embodiments of the invention, to providing SVT discrimination capability to certain devices jointly configured for both cardiac contractility modulation (CCM) therapy and operation as an ICD device. This is further explained, for example, in relation to FIGS. 1D-4, herein. Sensing electrodes (of the electrode sets) optionally include electrodes which are also used for the application of therapy, for example, CCM therapy. In some embodiments, one or both of the ventricular electrode sets (or another electrode set which uses one or more electrodes from the first and second ventricular electrode sets) is also used in the ICD sensing of block 151.

Optionally, one lead (e.g., a lead positioned to extend in along a superior-inferior axis of the ventricular septum) comprises the ventricular electrode sets.

While two electrodes may establish a bipolar configuration that provides near-field sensing, optionally more than two sensing electrodes are used in a near-field sensing configuration. Herein the term "bipolar" is used to indicate electrode sets comprising at least two sensing electrodes.

As is further explained, for example, in relation to block 156, differences (e.g., timing differences) in electrical signals in a plurality of ventricular heart wall regions are analyzed to determine information about the nature of a potential arrhythmia. In some embodiments, the ventricular locations are separated by about 1 cm, 1.5 cm, 2 cm, 2.5 cm, 3 cm, or another distance. Assuming the event detection order A-then-B (block 150, then block 154), the identities of the "first" and "second" bipolar arrangements could be different depending on the direction of depolarization wavefront propagation (e.g., anterograde or retrograde propagation of through a ventricular septum).

The determination of block 155 is made on the basis of the ICD sensing data categorization at block 153. Several different methods exist for performing this categorization. However, these methods potentially, although inappropriately, include categorization of arrhythmias due to SVT as candidates for defibrillation.

If a detected heart arrhythmia is not a candidate condition for defibrillation (based on the ICD sensing data), then the flowchart may return to the start, where the ICD sensing of block 151 and event detection 150, 154 restart.

If the detected heart arrhythmia is a candidate for defibrillation, the flowchart proceeds to block 156. At block 156, analysis of events A and B is performed to determine whether or not the candidate arrhythmia is actually appropriate for defibrillation, by categorizing the arrhythmia as due to supraventricular tachycardia (SVT), or not.

In general, the relative timing of the sensing of events A and B may be interpreted as indicating the direction and speed of depolarization wavefront passage between the positions of the first and second electrode sets. The wavefront (or rather, at least a directional component of the wavefront) passes in the direction between the earlier-sensing electrode position and the later-sensing electrode position, at a velocity indicated by the ratio of their distance to their relative delay. Based upon this indicated direction and speed, transmission may be interpreted as being initiated from the atrium (that is indicative of SVT), or from the ventricle. Examples of algorithms for performing the categorizing are described, for example, in relation to FIGS. 5A-5E, herein.

In some embodiments, the determinations at blocks 155, 156 are part of the operations of blocks 164 and/or 166 of FIG. 1A.

It should be understood that direction and speed categorization of events A and B at block 156 is not necessarily subsequent to determination at block 155 of an arrhythmia as a candidate for defibrillation. The ordering shown in FIG. 1A is for purposes of description. It should also be understood that the two processing streams are optionally interconnected in way other than shown in FIG. 1A, but leading to the same result. For example, the determination of block 156 optionally is used to suppress ICD sensing and/or categorization, effectively leading to a suppression of defibrillation shock delivery before any ICD candidate (block 155) can be determined.

If the determination at block 156 is that events A, B do not indicate SVT as the category of the arrhythmia, then, at block 158 (corresponding, in some embodiments, to block 168 of FIG. 1A), at least one defibrillation shock is delivered to the heart. Otherwise, defibrillation is aborted. In either case, the flowchart then returns to the beginning again.

Device of Discriminating SVT-Type Arrhythmia

Reference is now made to FIG. 1B, which is a block diagram that schematically represents an ICD device 170 configured to discriminate SVT-type arrhythmias based on inputs from two ventricular electrode sets 103, 105.

Block 174 represents a detector configured to detect arrhythmias (e.g., corresponding to the actions of blocks 151, 153, 155 of FIG. 1A) which are candidates for correction by the administration of a defibrillation shock by defibrillation circuit 176. Sensed data used to perform this detection optionally come from one or both of ventricular electrode sets 103, 105. Block 172 represents an SVT discriminator configured to perform the operations of blocks 150, 154, and 156 of FIG. 1A.

In some embodiments, ICD device 170 is a dual- or multi-function device, for example, a combined ICD and CCM therapy device; a combined ICD and cardiac resynchronization therapy (CRT) device; an ICD device combined with another device such as a vagus nerve, baroreceptor, or other neurostimulator; or another implantable heart device. In some embodiments, three or more functions (for example, selected from those just listed) are combined. A combined ICD/CCM therapy device is described in relation to FIG. 4.

Implantable Pulse Generator

Figures 1D, 2:
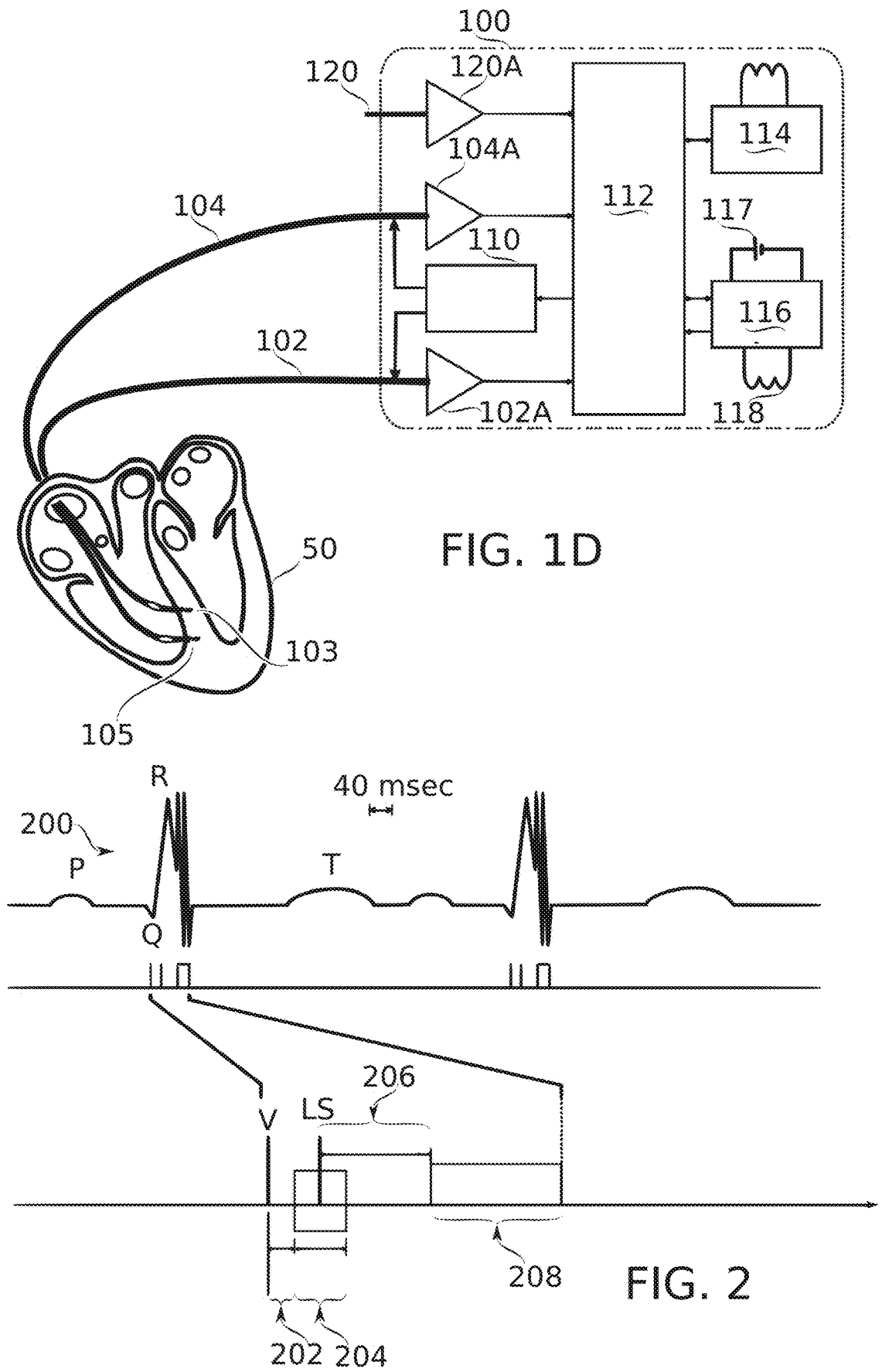
FIG. 1D schematically illustrates an implantable pulse generator (IPG) connected to the heart via two bipolar leads anchored to the right ventricular septum, according to some embodiments of the present invention.
FIG. 2 schematically represents operation of a "windowing" algorithm of an IPG, according to some embodiments of the present disclosure.

Reference is now made to FIG. 1D, which schematically illustrates an implantable pulse generator (IPG) 100 connected to the heart via two bipolar leads 102, 104 anchored to the right ventricular septum, according to some embodiments of the present invention. Principles of the operation of this device serve as a background for explaining features (presented in relation to FIG. 4) that provide SVT-discriminating ICD to a modified version of IPG 100.

IPG 100 is an example of a device configured for a non-ICD function such as delivery of CCM therapy. The IPG 100 shown optionally represents, for example, Impulse Dynamics' OPTIMIZER SMART Implantable Pulse Generator (IPG) for the delivery of CCM therapy. The OPTIMIZER SMART IPG continuously monitors a heart's intrinsic activity and generates CCM signals in synchrony with detected local electrical activity, such that their delivery happens during the ventricular absolute refractory period.

The OPTIMIZER SMART IPG incorporates two ventricular sense amplifiers 102A, 104A that detect ventricular activation from IEGMs picked up by ventricular leads 102, 104 attached (at positions 103 and 105, respectively) to the right ventricular septum of heart 50. Optionally, leads 102, 104 are separated by at least 1 cm, 2 cm, 3 cm, 4 cm, or another distance. Sensed and amplified ventricular activation signals are transmitted to controller 112. Optionally, one or more addition leads 120 are connected to another position on the heart 50, for example, an atrial position.

Optionally amplifier 120A transmits sensed and amplified activation signals to controller 112. Controller 112 is configured to activate CCM generator 110 to generate a return signal through leads 102, 104, to affect heart contractions, for example as described herein in relation to FIGS. 2-3B.

Also shown are battery recharge and power regulation circuit 116, including rechargeable cell 117 (optionally a lithium ion cell) and receiver coil 118; and inductive communication and telemetry circuit 114.

Reference is now made to FIG. 2, which schematically represents operation of a "windowing" algorithm of an IPG 100, according to some embodiments of the present disclosure.

In some embodiments, a control algorithm of IPG 100 implemented by controller 116 enables the delivery of CCM signals via CCM generator 110 to the heart on a certain heartbeat if an appropriate intraventricular activation sequence and timing is detected between ventricular-septum IEGM signals sensed through leads 102, 104.

Trace 200 represents events corresponding to cardiac cycles not classified as abnormal (e.g., not subject to excessive noise or ventricular tachycardia). Upon sensing a ventricular event V (e.g., onset of the Q and/or R waves measured by lead 102), controller 116 opens a local sense alert window 204, optionally after some initial delay 202.

The alert window can be inside the AV interval (between P and R), inside the VA interval (outside the AV interval), or partially inside the AV and partially inside the VA interval. For example, the position 204 in time of alert window is determined, in some embodiments, by two programmable parameters:

Alert Start Length of delay 202 that begins with the right ventricular event V (e.g. detected by lead 102).

Alert Duration of the alert window 204.

Width

In some embodiments, the first local sense event detected within the alert window 204 (e.g. at LS, representing the time of a locally sensed event sensed by lead 104) serves as a trigger for potential CCM signal delivery. When an event is detected, the alert window 204 is immediately terminated.

From this moment of the heartbeat cycle, otherwise valid locally sensed events detected by lead 104 but outside the alert window are considered to be premature ventricular contractions (PVCs). These optionally inhibit CCM signal delivery, e.g., for a programmable number of cycles.

If not inhibited, CCM delivery occurs during period 208, optionally after a post-sensing delay 206.

The "windowing" algorithm using the two bipolar leads 102, 104 effectively implements a conduction velocity filter, whereby only beats for which the depolarization wavefront propagates in a certain direction and at a certain velocity qualify said beat as suitable for the delivery of a CCM signal.

Figures 3A, 3B:
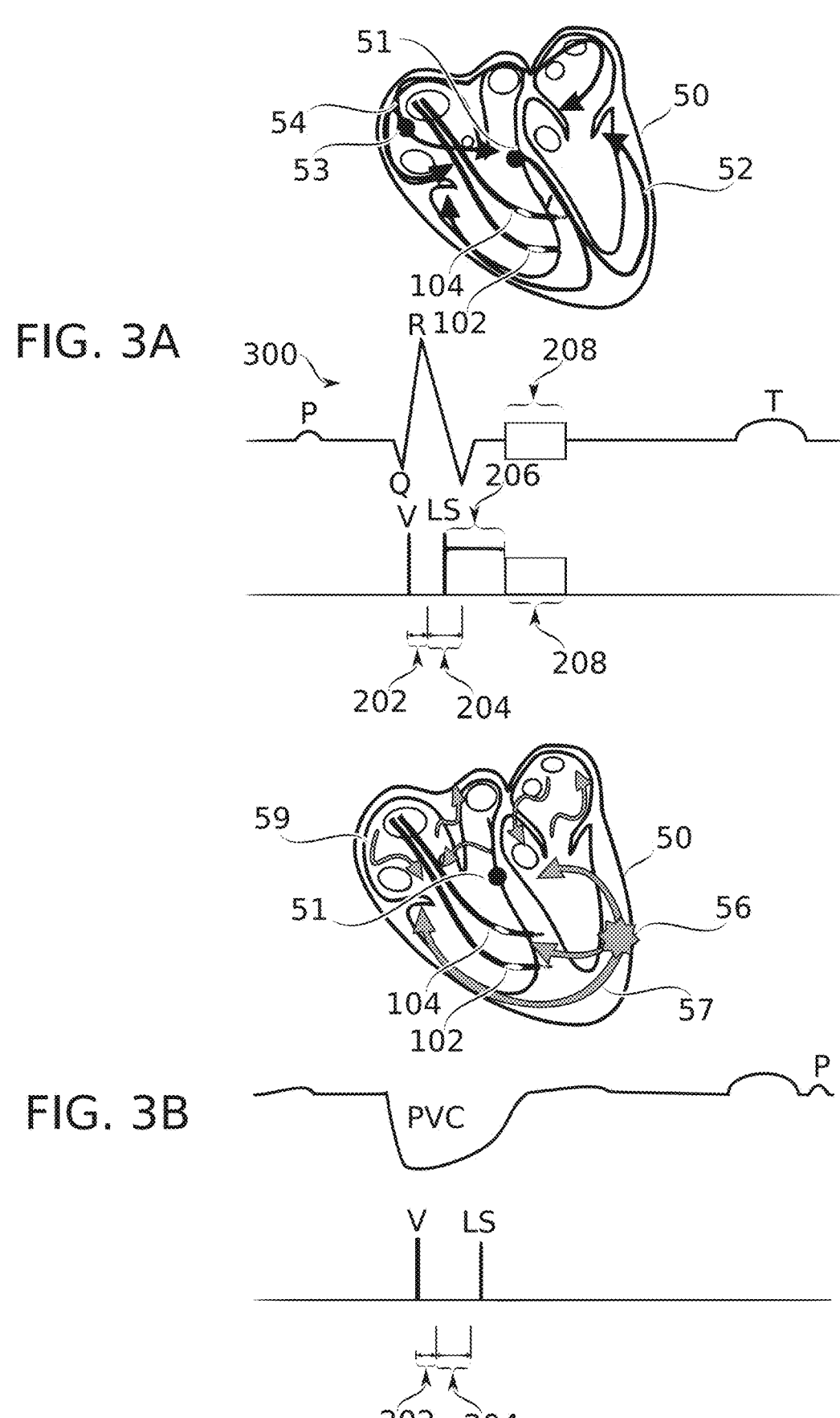
FIGS. 3A-3B schematically indicate discrimination by a conduction velocity filter between normally-conducted beats and ventricular ectopic beats, according to some embodiments of the present disclosure.

Reference is now made to FIGS. 3A-3B, which schematically indicate discrimination by a conduction velocity filter between normally-conducted beats and ventricular ectopic beats, according to some embodiments of the present disclosure. In some embodiments, the discrimination is used to deliver a CCM signal only on normally-conducted beats. FIG. 3A shows a normally-conducted beat condition in a heart 50. The beat is initiated from sinoatrial (SA) node 53, arriving at atrioventricular (AV) node 51 via atrial conduction pathways 54, and then propagated from AV node 51 along ventricular conduction pathways 52. Trace 300 indicates landmark electrical events during the heartbeat cycle, with the initial delay 200, alert window 204, post-sensing delay 206, and CCM delivery period 208 shown as described in relation to FIG. 2.

FIG. 3B shows one type of potential arrhythmia, involving ectopic ventricular pulse initiation from region 56 along ventricular conduction pathways 57, and disorganized atrial conduction along arterial conduction pathways 59. This type of arrhythmia is a potential candidate for correction by administration of a defibrillation shock, e.g., using a dual CCM/ICD device such as that now described in relation to FIG. 4.

Figure 4:
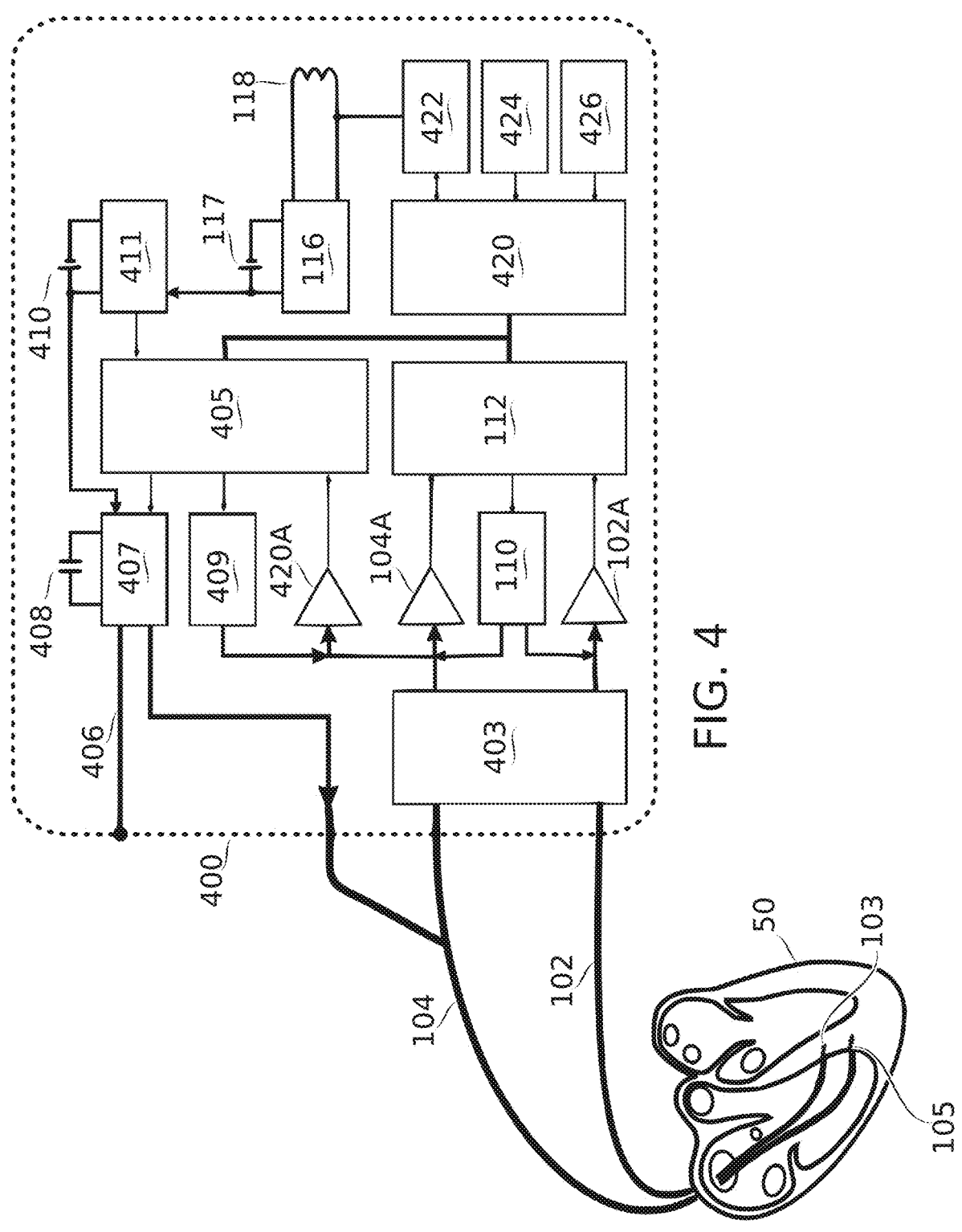
FIG. 4 schematically illustrates a block diagram of an IPG configured for delivering both CCM and ICD therapies.

Reference is now made to FIG. 4, which schematically illustrates a block diagram of an IPG 400 configured for delivering both CCM and ICD therapies. IPG 400 furthermore implements SVT vs. VT discrimination based on analysis of the propagation time and propagation paths of depolarization wavefronts, according to some embodiments of the present disclosure. Potentially, SVT vs. VT discrimination helps to reduce the incidence of unnecessary shocks.

In some embodiments, two electrogram signals are sensed from the bipolar electrode pairs of the CCM lead 102 (optionally equivalent to lead 102 of FIG. 1D) and the ICD lead 104 (optionally equivalent to lead 104 of FIG. 1D). These signals are amplified and detected by sense amplifiers 102A, 104A. These amplifiers have timing resolution sufficient to measure different wavefront arrival times at the bipolar electrode positions 103, 105. Optionally, this is achieved by using a relatively high-frequency bandpass (e.g. 70-200 Hz). The measuring rate and inter-channel timing and sequencing is used by CCM controller 112 to control CCM generator 110 to deliver CCM signals (e.g., to the right ventricular septum) via the same electrodes of the leads as described, for example, in FIGS. 2-3B.

In some embodiments, a separate ICD sense amplifier 402A, which optionally has with a bandpass like that of a conventional ICD device (e.g. within a range of 8-40 Hz) detects intracardiac events that are used by a prior-art ICD algorithm running in ICD controller 405 to detect tachyarrhythmias. Before a defibrillation, however, the method of FIG. 1A is used to evaluate whether or not the tachyarrhythmia may be the result of rapid supraventricular activity (for which a shock is unnecessary) or a re-entrant loop within the ventricles (which should be treated with a shock).

To perform the discrimination, the wavefront conduction velocity (direction and speed of the propagating depolarization wave) measured from the IEGMs picked-up by the two bipolar pairs and analyzed by the CCM controller 112 is communicated, e.g., on a beat-to-beat basis, to the ICD controller 405.

Also shown in FIG. 4 are optional pacing pulse generator 409, and defibrillation pulse generator 407 comprising defibrillation capacitors 408 configured to charge with energy (e.g., about 36 J of energy) before delivery of a defibrillation shock. Other circuits of IPG 400 include, in some embodiments, defibrillation battery 410 and battery management circuit 411; rechargeable cell 117, charging/power regulation 116, and receiver/communications coil 118; and high voltage isolation circuit 403. Housekeeping circuitry 420 manages functions such as inductive charger/communication circuit 422, magnetic sensor 424, and/or temperature sensor 426.

Discrimination of Conduction Patterns

Reference is now made to FIGS. 5A-5D, which schematically illustrate discrimination of conduction patterns passing through a ventricular septum, according to some embodiments of the present disclosure.

Shown in each of FIGS. 5A-5D are leads 102, 104 positioned in a septum of heart 50, and sensing (electrode) positions 511A, 512A. Also shown are different estimates of intraseptal conduction vector 515, which varies in direction and length depending on the apparent direction and speed of wavefront conduction between sensing positions 511A and 512A.

In the timelines at the bottom of each of FIGS. 5A-5D, marks 511, 512 represent the times at which a conduction wavefront reaches sensing position 511A and 512A, respectively. Time range 513, in some embodiments, represents a discrimination window, used to discriminate certain supraventricular tachycardias from true-ventricular tachycardias.

In some embodiments of the invention, a first division of normal and abnormal sinus rhythms may comprise orthodromic (e.g., FIGS. 5A, 5C) and antidromic (e.g., FIGS. 5B, 5D) conduction through the ventricular septum.

Consistent with orthodromic conduction through the septum as shown in FIG. 5A in particular, normal sinus rhythm, as well as the following SVTs, are conducted to the ventricle in an orthodromic direction (i.e., conduction vector 515 from wavefront position 510A toward wavefront position 510B) through the normal conduction apparatus (Bundle of His and Purkinje Fibers) within the ventricular septum:

Atrial tachycardia
Atrial flutter
Atrial fibrillation
Atrio-ventricular nodal re-entrant tachycardia (AVNRT)
Orthodromic Wolf-Parkinson-White atrioventricular re-entrant tachycardia (Orthodromic WPW-AVRT)

True-ventricular tachycardias, on the other hand, are conducted through the conduction system in an antidromic direction, and/or produce disturbances within the conduction system itself. For example, in FIG. 5B, conduction is antidromic from wavefront position 510C toward wavefront position 510D. In FIG. 5D, conduction comprises an antidromic component as the wavefront moves between wavefront position 510H and wavefront position 510G. Conduction in FIG. 5C is orthodromic, but moves from wavefront position 510E toward wavefront position 510F, rather than originating supraventricularly.

In some embodiments, shock delivery for rhythms classified by a conventional ICD algorithm as tachycardia would be inhibited (or at least delayed) whenever the intraseptal conduction velocity and/or conduction direction reported by the CCM controller 112 demonstrates that orthodromic conduction direction and speed fall within a predefined range. This would potentially reduce the incidence of unnecessary shocks to be delivered to a patient due to the majority of SVTs.

The timelines of FIGS. 5A-5D represent an example of how this may be implemented, in some embodiment of the invention. In each of FIGS. 5A-5D, mark 511 falls either within (FIG. 5A) our outside of (FIGS. 5B-5D) discrimination window 513. Discrimination window 513, in some embodiments, has a predetermined duration, and a predetermined onset delay from the detection of mark 512. Optionally, discrimination window 513 onset and/or duration parameters are controlled by predetermined constants. Optionally, discrimination window 51 onset and/or duration parameters are determined, for example as described in relation to FIG. 6. In some embodiments, discrimination window 513 has an onset after wavefront detection at sensing position 512A of, for example, between about 0-100 msec. In some embodiments, the onset is between about 0-50 msec. In some embodiments, discrimination window 513 closes about 1-75 msec after it begins. In some embodiments, the discrimination window 513 closes about 1-40 msec after it begins. It should be understood that the time periods before and/or after discrimination window 513 are optionally themselves also distinguished from one another, and optionally sub-divided; e.g., to allow distinguishing different wavefront origins, for example as illustrated and/or described in relation to FIGS. 5A-5D. Optionally, inputs are provided to a therapeutic device additional and/or alternative to a shock defibrillator, e.g., to modulate delivery of pacing and/or inhibitory electrical pulse(s).

Optionally, these parameters are adjusted, e.g., depending on the recent heart rate, duration of tachycardia, or another parameter. For example, a condition for delivering ICD at all may be that the heart rhythm frequency is within a particular range. SVT detection parameters may, moreover, be adjusted for different ranges of heart rhythm frequency. For example, in a normal sinus rhythm rate zone (e.g., between about 60-160 bpm), the device is optionally disabled from delivering ICD therapy. In a range associated with potential ventricular tachycardia (for example between about 160-240 bpm), the windowing algorithm could be activated; optionally with a window wide enough that the device would err more on the side of inhibiting the therapy (shock delivery, possibly after attempting anti tachycardia pacing) than in the case of fast ventricular tachycardia. In a range associated with fast ventricular tachycardia (for example, between 240-300 bpm), the inhibition window is optionally programmed to be narrower (shorter in milliseconds, and/as a percent of to the length of the heartbeat cycle). Above 300 bpm, the windowed discrimination algorithm is optionally not used to determine whether ICD should be delivered.

When mark 511 falls within discrimination window 513, in some embodiments, this is considered an indication that the tachycardia is supraventricular in origin, and ventricular defibrillation is suppressed.

The in-window/out-of-window result determining an SVT origin of an arrhythmia is optionally applied to suppress defibrillation in different ways. In some embodiments, the operation of an ICD algorithm is prevented by the discrimination of SVT. In some embodiments, the ICD algorithm operates independently, but any determination by the algorithm to begin defibrillation is ignored in the case of SVT. Optionally, the ICD algorithm itself is modified to perform the SVT determination and modify its output accordingly. Optionally, the SVT determination is only triggered when arrhythmia is already determined to have begun, e.g., activated by a result of the ICD algorithm, and/or activated by an earlier pattern of sensing data which is consistent with an initiating and/or ongoing pattern of arrhythmia. Optionally, detection of SVT is used to trigger a non-defibrillating therapy. Optionally, suppression of defibrillation after determining an SVT origin of an arrhythmia is itself suppressed by a further input, e.g., a time and/or heartrate dependent input.

The windowing algorithm is explained herein for purposes of illustration. It has the potential advantage of being calculable with a minimum of computational resources, and/or implemented by analog timing circuitry. The same defibrillation suppression outcome can be obtained in another fashion. For example, in some embodiments, apparent speed and direction of the conduction vector 515 are explicitly determined, and a conduction vector which falls within a certain parameter range for its speed and direction is taken as an indication that any current arrhythmia is due to SVT.

Figure 5E:
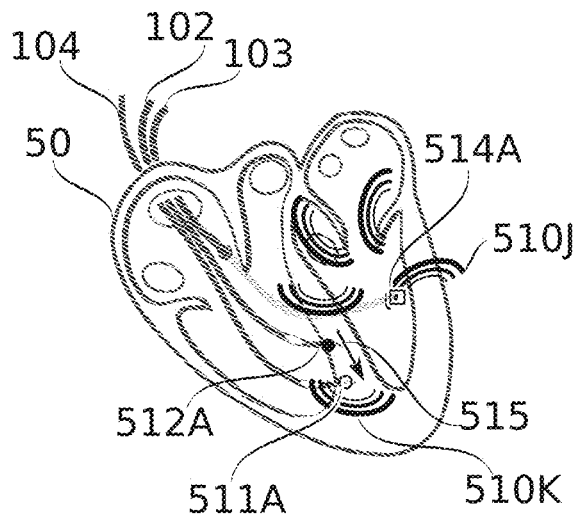
FIG. 5E schematically illustrates three-sensor discrimination of conduction patterns passing through a ventricular septum, according to some embodiments of the present disclosure.
Figure 5E:
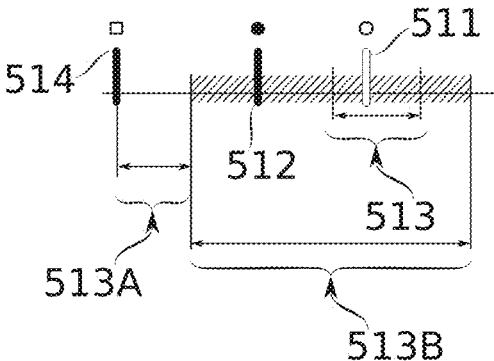

Reference is now made to FIG. 5E, which schematically illustrates three-sensor discrimination of conduction patterns passing through a ventricular septum, according to some embodiments of the present disclosure.

Two remaining forms of arrhythmia—antidromic Wolf-Parkinson-White atrioventricular re-entrant tachycardia (antidromic WPW-AVRT) and Wolf-Parkinson-White atrial fibrillation (WPW-AF)—comprise SVTs which potentially cannot be discriminated from true ventricular tachycardias through an analysis of the conduction speed and direction of the depolarization wavefront sweeping the ventricular septum alone.

Shown in FIG. 5E in addition to leads 102, 104 positioned in a septum of heart 50 is a third lead 103, positioned in another ventricular region. Lead 103 is shown entering heart 50 through the same blood vessel (e.g., the superior vena cava) as leads 104, 102; however, it is optionally routed from another direction. To sensing (electrode) positions 511A, 512A, is thereby added a third sensing position 514A, corresponding to the position of the electrode of lead 03. In some embodiments, lead 103 is an LV lead, for example as used in cardiac resynchronization therapy (RCT); e.g., a lead passing along the coronary sinus. In some embodiments, lead 103 is a lead placed in the apex of the left atrium.

In this instance, the estimate of intraseptal conduction vector 515 appears indistinguishable from normal orthodromic conduction, and indeed mark 511 on the timeline for FIG. 5E falls within discrimination window 513. This could potentially result in a determination that any concurrent tachycardia is supraventricular in origin.

However, in some embodiments, detection of a conduction wavefront passing through sensing position 514A results in the activation of a predetermined suppression window 513B. Suppression window 513B suppresses the defibrillation discrimination function of discrimination window 513, with the result that defibrillation is not suppressed, even though mark 511 falls within the period which would otherwise result in the prevention of delivery of a defibrillation shock.

The suppression window 513B, in some embodiments, is long enough to cover the time it takes for conduction to pass circuitously between wavefront position 510J and wavefront position 510K, but not so long that it would potentially suppress discrimination of SVT (e.g., about 100-250 msec, or another suitable duration). Optionally, suppression window 513B begins after delay 513A (e.g., of about 1-50 msec). The delay 513A, in some embodiments, is set to be long enough, e.g., so that an atrially originating wavefront arriving first at sensing position 514A and then, a few milliseconds later, at e.g., sensing position 512A is not confused with a ventricular origin of wavefront initiation. In some embodiments, suppression window 513B may itself be suppressed, for example, if there is a detection of a conduction wavefront passing sensing position 512A just before, or within a sufficiently short time period after a wavefront passes position 515A.

Figure 6:
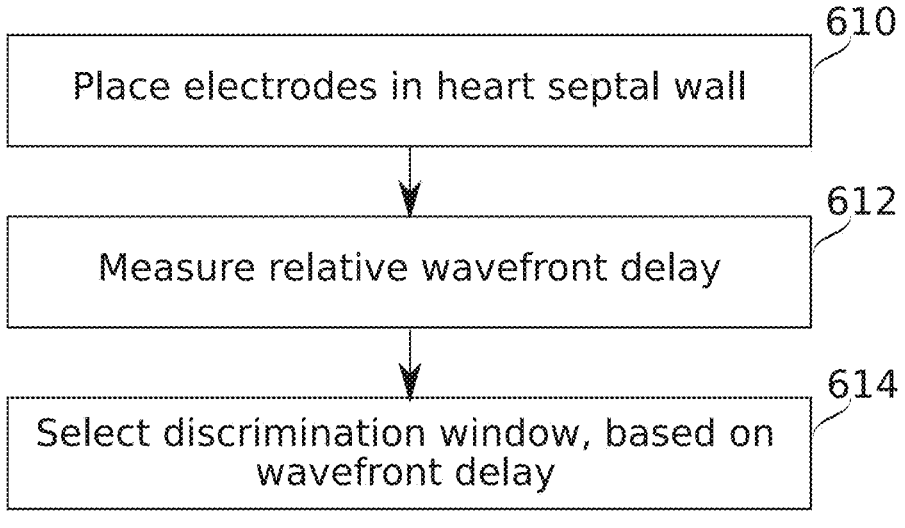
FIG. 6 is a flowchart representing a method of selecting a discrimination window, according to some embodiments of the present disclosure

Reference is now made to FIG. 6, which is a flowchart representing a method of selecting a discrimination window 513, according to some embodiments of the present disclosure. As described, for example, in relation to FIGS. 5A-5E, relative delays between a first and second electrode falling within discrimination window 513 are optionally classified as indicating a supraventricular (e.g., atrial) origin of the impulse that is triggering the heartbeat. When the heartbeat occurs during a period of tachyarrhythmia, this indication is optionally used to distinguish SVT from VT.

At block 610, in some embodiments, a plurality of electrodes is placed in the heart septal wall, for example as illustrated and/or discussed in relation to FIGS. 1D and/or FIGS. 5A-5E. The precise placement of the electrodes, optionally including their relative placement superior or inferior to each other is not necessarily fully known ahead of their implantation. Furthermore, the rate of electrical conduction of electrical activity wavefronts between positions of the electrodes is not necessarily fully known ahead of their implantation. Accordingly, the optimal positioning of discrimination window 513 is, in some embodiments, determined based on measurements made indicative of the actual electrode configuration after implantation.

At block 612, in some embodiments, a relative delay in heart electrical activity wavefronts reaching the plurality of electrodes is measured. This can be performed in different ways. Optionally, the relative time of arrival of an R-wave component of a heart ECG is measured at each of the plurality of electrodes. The R-wave component has potential advantages for this use insofar as it is relatively large in amplitude and relatively fast; however, any other component of the ongoing cycling heart electrical activity waveform is used additionally or alternatively to the R-wave. The relative delay is measured, for electrical impulses having an atrial origin, e.g., an origin from a normal AV node activation, an atrially paced activation, or another atrial origin. The normal heart rate relative wavefront delay is optionally considered to be representative of relative wavefront delay which would also occur during a putative future episode of SVT. Additionally or alternatively, atrially paced activation is repeated at a rate which simulates SVT.

The relative time of arrival can be measured any suitable number of times, e.g., to allow calculation of a statistical representation of the normal relative time of waveform arrival at the sites of electrode implantation. Optionally, the statistical representation comprises an average delay, and a standard deviation of that delay. Optionally, measurements of relative delay are performed at a plurality of heart rates. Information obtained from these measurements is also referred to herein as calibration information. For example, the calibration information indicates a direction of an electrical wavefront to be atrial-to-ventricular when the electrical wavefront reaches a second electrode after reaching a first electrode, with a delay which is also characteristic of a first-to-second electrode delay of wavefronts known from the measurements of block 612 to be atrially activated.

At block 614, in some embodiments, a discrimination window is selected, based on the wavefront delay measurements (calibration information) of block 612. In some embodiments (e.g., for a generally Gaussian distribution of relative delays), the window is selected as a range of delays within ±2, ±3, ±4 or another number of standard deviations of the average delay. Optionally, the window size and offset is selected to include all measurements of relative time of arrival, or at least a great majority of the measurements, e.g., at least 99% of measurements, or at least 99.9% of measurements. Optionally, the selected discrimination window is dynamic and heart rate dependent, and/or selected according to a current heart rate; for example, to account for potential differences in wavefront velocity as a function of heart rate. Heart rate adjustment of the window is optionally performed based on measurements of delays at different heart rates (e.g., as described in relation to block 612). Optionally, heart rate adjustment of the window is performed based on a standard derived from patient population observations.

Accordingly, a subsequently measured delay falling within this range of delays is likely to be indicative of an electrical wavefront which originates atrially. In some embodiments, this range of delays is used to set discrimination window 513, for example as described in relation to FIGS. 5A-5E. In some embodiments, whether or not a delay falls within a discrimination window 513 is used to set an input to an implanted heart device; e.g., an input which suppresses delivery of defibrillation shock therapy.

GENERAL

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

In addition, any priority document(s) of this application is/are hereby incorporated herein by reference in its/their entirety.

What is claimed is:

1. An implantable cardioverter defibrillator device (ICD) comprising:

at least two sensing electrode pairs, said at least two sensing electrode pairs are arranged to be located within the same ventricular region of the heart, wherein each of said at least two sensing electrode pairs is positioned on a separate lead, wherein the ICD is configured to:

sense, during a cardiac arrhythmia in a heart and within the interval of a heartbeat, times of electrical wavefront arrival in at least two ventricular locations of the heart, wherein each of said at least two ventricular locations is defined by the location of said sensing electrode pair;

generate a direction indication based on said sense, and suppress production of defibrillation shocks by the defibrillator in response to the cardiac arrhythmia, based on said direction indication of wavefront travel indicated by the relative timing of the sensing at the at least two ventricular locations.

2. The device of claim 1, wherein the at least two sensing electrode pairs are configured to be positioned at different locations along a superior-inferior axis within a ventricular septum, and the ICD suppresses production of defibrillation shocks based on the direction of wavefront travel indicated when the electrical wavefront is sensed to arrive at the more superior location before arriving at a more inferior location.

3. The device of claim 2, comprising a sensing electrode configured to be positioned in a non-septal location of the ventricles.

4. The device of claim 3, configured so that the production of defibrillation shocks is not suppressed if the sensing electrode configured to be positioned in a non-septal location of the ventricles senses electrical wavefront arrival within a predetermined interval before the ICD senses arrive of the electrical wavefront at a ventricular septum location.

5. The device of claim 1, comprising a controller configured to:

distinguish between transmission of the wavefront being initiated from the atrium and transmission of the wavefront being initiated from the ventricular based on direction of the wavefront passing between a first and second electrode pair of said at least two sensing electrode pairs;

distinguish between a supraventricular tachycardia and a ventricular tachycardia based on the transmission of the wavefront being initiated from the atrium or from the ventricular; and wherein said configuration to suppress production of defibrillation shocks uses a direction calculated with reference to a known direction of a joining axis between the at least two locations in the heart, and wherein the at least two sensing electrode pairs are configured to be positioned by separate leads at different locations within the right ventricle.

6. The device of claim 1, wherein said device includes a cardiac contractility modulation functionality that delivers cardiac contractility modulation therapy using said separate lead which comprises said sensing electrode pair.

7. A method of setting a discrimination window to an implanted heart device distinguishing SVT from VT, comprising:

(i) measuring a relative delay in electrical wavefront arrival for a plurality of electrodes implanted in the ventricular septum, wherein each of the plurality of electrodes comprises a sensing electrode pair, each of said sensing electrode pair is positioned on a separate lead, wherein the electrical wavefront is initiated from an atrial location;

(ii) generating a direction indication of said electrical wavefront from said atrial location, and (iii) setting the window, based on the measured relative delay and the generated direction indication, wherein the implanted heart device is configured to apply antiarrhythmic therapy, and comprising configuring, using the discrimination window, the implanted heart device to apply the antiarrhythmic therapy or to avoid application of the antiarrhythmic therapy.

8. The method of claim 7, wherein the implanted heart device comprises a defibrillator, and comprising configuring the defibrillator for production of defibrillation shocks using the provided input.

9. The method of claim 7, wherein said input is based on a single wavefront propagation measurement and is applied for a cardiac cycle in which said measurement is made.

10. A method of providing an input to an implanted heart device in response to a heart arrhythmia, the method comprising:

sensing, during a cardiac arrhythmia in a heart, a direction of electrical wavefront passage through a ventricular region of the heart, wherein the direction of the electrical wavefront is determined by sensing relative timing of the passage of the electrical wavefront through a plurality of separate locations within said ventricular region of the heart, wherein each of the plurality of separate locations is defined by the location of an electrode pair used to perform the sensing, each electrode pair is positioned on a separate lead;

generating a direction indication based on said sensing, generating an input based on the direction indication of the electrical wavefront, which input can be used to distinguish between types of cardiac arrhythmia; and providing the input to the implanted heart device, wherein the implanted heart device is configured to apply antiarrhythmic therapy, and comprising configuring, using the provided input, the implanted heart device to apply the antiarrhythmic therapy or to avoid application of the antiarrhythmic therapy.

11. The method of claim 10, wherein the implanted heart device is configured to apply antiarrhythmic therapy, and comprising configuring the implanted heart device to apply the antiarrhythmic therapy using the provided input.

12. The method of claim 10, wherein the implanted heart device comprises a defibrillator, and comprising configuring the defibrillator for production of defibrillation shocks using the provided input.

13. The method of claim 10, wherein the sensing comprises using calibration information to determine the direction of electrical wavefront passage.

14. The method of claim 10, wherein the ventricular region of the heart comprises a ventricular septum.

15. The method of claim 10, further comprising preventing production of defibrillation shocks when the sensed direction of electrical wavefront passage indicates that the electrical wavefront is traveling in a direction from the atria and toward the ventricles.

16. The method of claim 10, wherein:
the provided input is an indication to the implanted heart device to configure application of antiarrhythmic therapy based on the relative timing of the relative passage of the electrical wavefront through the plurality of separate locations within said ventricular region of the heart.

17. The method of claim 16, wherein the plurality of separate locations within said ventricular region comprise two locations along a ventricular septum.

18. The method of claim 17, wherein the plurality of separate locations within said ventricular region comprises a non-septal location in the ventricles.

19. The method of claim 16, wherein the implanted heart device is an at least dual function device.

20. The method of claim 16, wherein the implanted heart device comprises a cardiac contractility modulation (CCM) therapy device.

21. The method of claim 16, wherein the direction of the electrical wavefront is in a direction from the atria and toward the ventricles, and the input is used to suppress delivery of the antiarrhythmic therapy.

22. The method of claim 10, wherein said input is based on a single wavefront propagation measurement and is applied for a cardiac cycle in which said measurement is made.

23. The method of claim 10, wherein said cardiac arrhythmia is an SVT and said input indicates one or both of avoiding a defibrillation shock and providing a treatment other than shock therapy.

24. The method of claim 10, further comprising determining to trigger a non-defibrillating therapy.

25. The method of claim 10, wherein each of said electrode pair is in contact with a cardiac tissue.

26. The method of claim 10, wherein each of said electrode pair is suitable for stimulating in response to said heart arrhythmia.

27. The method of claim 10, wherein the electrical wavefront is detected locally.

28. The method of claim 10, further comprising determining, based on said input, to apply an antiarrhythmic therapy, modify said antiarrhythmic therapy or suppress delivery of said antiarrhythmic therapy.

29. The method of claim 10, wherein said direction indication is generated based on the sensed relative timing.

30. The method of claim 10, wherein said direction indication is an indication that the electrical wavefront is traveling in a direction from the atria and toward the ventricles.

31. The method of claim 10, wherein the sensing and the generating the input is performed using the same implanted heart device.

* * * * *